United States Patent [19]

Larsson

[11] Patent Number: 4,481,657
[45] Date of Patent: Nov. 6, 1984

[54] PATIENT SUPPORT APPARATUS COMPRISING A ROTATABLE SUPPORT

[75] Inventor: Sten Larsson, Vällingby, Sweden

[73] Assignee: Siemens Aktiengesellschaft, Berlin & Munich, Fed. Rep. of Germany

[21] Appl. No.: 383,983

[22] Filed: Jun. 1, 1982

[30] Foreign Application Priority Data

Jun. 1, 1981 [DE] Fed. Rep. of Germany ....... 3121728

[51] Int. Cl.³ .......................................... G03B 41/16
[52] U.S. Cl. ...................................... 378/209; 378/91
[58] Field of Search .......................... 378/91, 196, 209

[56] References Cited

U.S. PATENT DOCUMENTS 3,848,132 11/1974 Foderaro ............................ 378/209
4,019,059 4/1977 Brundin ............................. 378/209

Primary Examiner—Craig E. Church
Attorney, Agent, or Firm—Hill, Van Santen, Steadman & Simpson

[57] ABSTRACT

In the case of a patient support apparatus, a support, rotatably mounted about a horizontal spatial axis, is height-, longitudinally- and laterally-adjustable relative to an x-ray apparatus, whereby at least the height adjustment proceeds by a motor. In order, in the case of a lengthwise displacement of the patient support, to automatically conduct such a height adjustment that the isocenter moves along a path—capable of being established in advance—along the support, it is provided in accordance with the disclosure that a processor constantly determines, for the actual coordinates of the spatial axis and of the tilt angle α of the support, the height of a desired examination point and compares it with the height of the isocenter. A follow-up control coupled with the processor ensures a constant adaptation of these two values.

10 Claims, 2 Drawing Figures

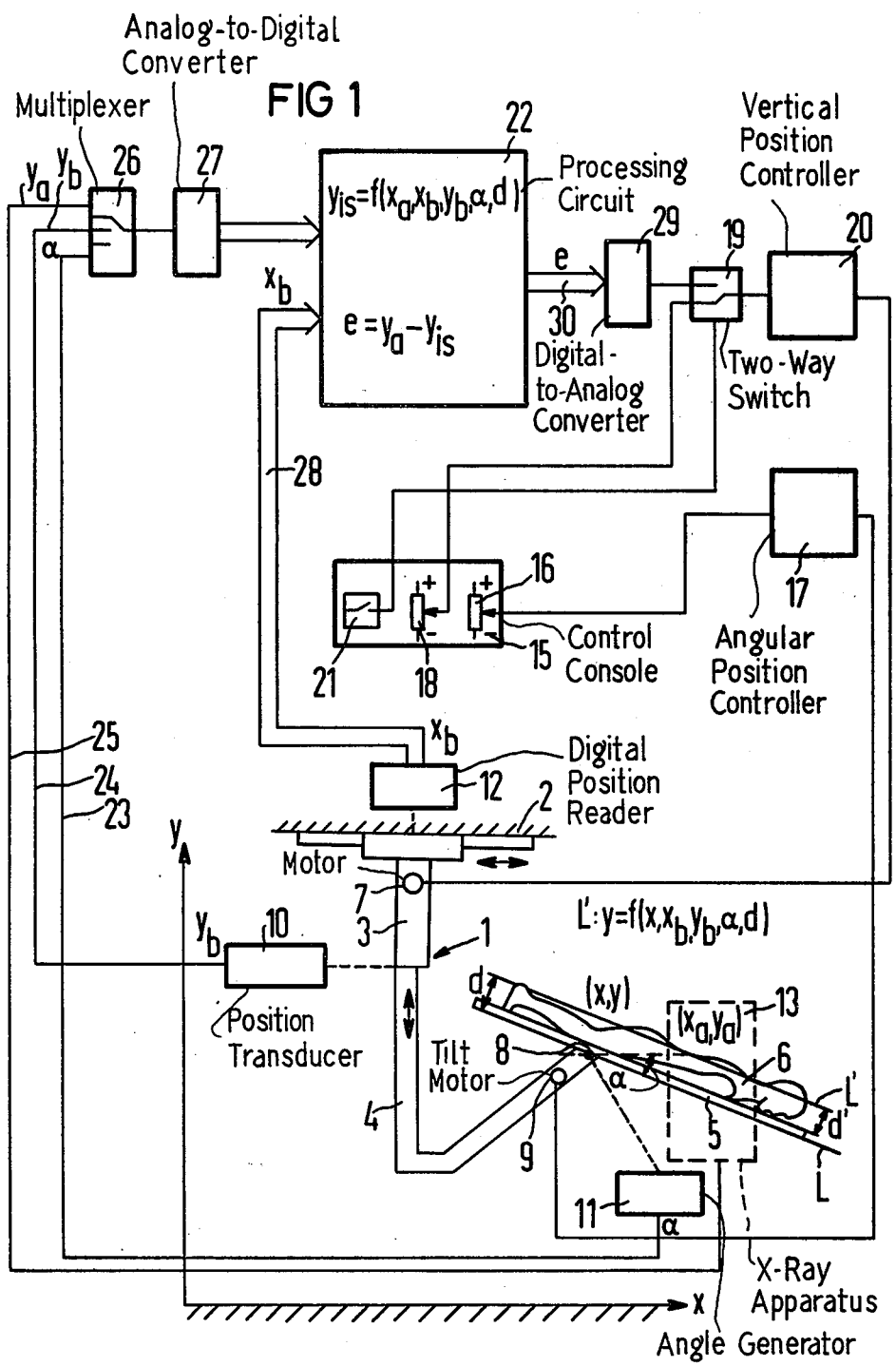

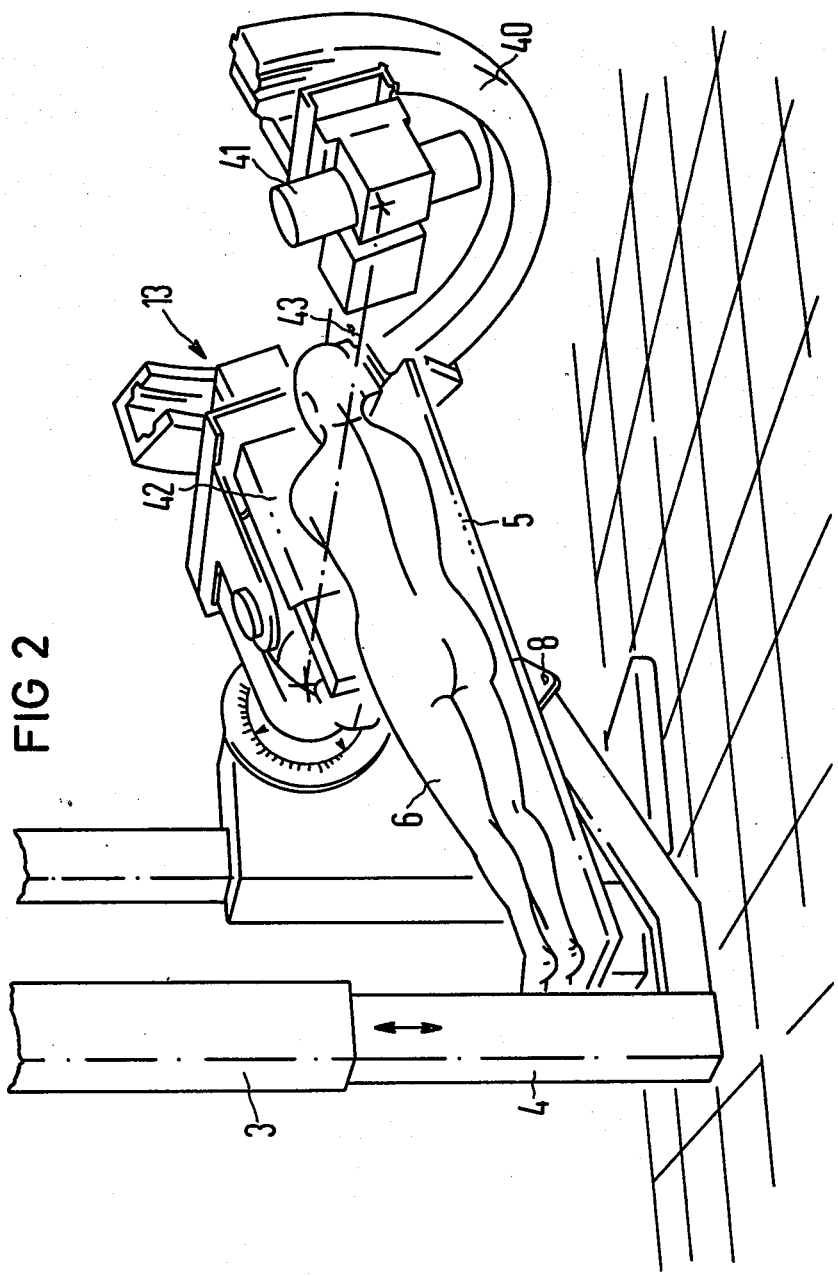

PATENT SUPPORT APPARATUS COMPRISING A ROTATABLE SUPPORT

BACKGROUND OF THE INVENTION

The invention relates to a patient support apparatus comprising a support which for positioning a patient resting on the support, is rotatable about a horizontal spatial axis, and is height-adjustable, longitudinally adjustable and laterally adjustable relative to an x-ray apparatus containing an x-ray source and an image detection device. A support apparatus of this type is, for example, known from the Elema-Schuml/o/ nander-Brochure Mimer III RCT-2, printed in Sweden 1969, or from the German No. AS 24 55 447. Both patient support apparatus serve the purpose of neuroradiological examinations which require an injection of contrast media into the fluid spaces, such as, for example, encephalography, ventriculography and myelography. Particularly in the case of these examinations it is decisive to follow the gravity-dependent contrast medium flow on an x-ray viewing screen. The contrast medium is injected into a spinal cord channel. If subsequently the patient is downwardly inclined with his head downwards, then the contrast medium runs in the direction of the head. If one inclines the patient subsequently in the other direction, then the contrast medium flows back again.

The patient support apparatus known from the German No. AS 24 55 447 renders possible an isocentric rotation of the support in order, for example, to direct the contrast medium flow. Particularly in the case of spinal column examinations, however, it is also necessary to follow the contrast medium flow over a comparatively long distance with a varying inclination of the patient, and such extensive contrast medium flow can only be partially detected with a fluoroscopic system. For a satisfactory examination it is desirable for the examination point in the body region of the patient to constantly be imaged at the center of the image detection device, i.e., at the isocenter.

SUMMARY OF THE INVENTION

In the case of a patient support apparatus of the type initially cited given a longitudinal displacement of the support apparatus carried out by an operator, an object underlying the present invention therefore resides in automatically conducting such a height adjustment that the isocenter traces a path—which can be established in advance—along the length of the patient support. Specifically, the isocenter (which may be a fixed point in space) is to trace a path relative to the support which coincides with a line parallel to the patient support and extending through a once-established (initial) treatment point. The relative movement of the isocenter thus is to be independent of the angular position of the support and hence of the inclination of the patient.

This object is achieved in accordance with the invention in that the patient support apparatus is provided with one each of an actual value transmitter for an x- and y-coordinate, respectively, of the horizontal spatial axis (rotational point of the support), as well as an angle generator system for sensing the tilting of the support relative to a horizontal axis, and that a control device is provided which, from these values and isocenter reference values $x_a$, $y_a$, representing the position of an isocenter, ascertains a signal for a follow-up control of the motor for the height adjustment which, upon occurrence of a difference between the reference and actual values with respect to the isocenter in the vertical or Y-direction ($y_a$, $y_{is}$), actuates the motor with the objective of achieving a compensation (reducing such difference to zero). (The actual value of the point associated with the table which is to be maintained coincident with the isocenter is established e.g. as lying on a parallel line at a distance d' from the surface at the support.)

The patient support apparatus has at least one motor for effecting the height adjustment of the support. The longitudinal displacement proceeds manually or by motor means. If a physician tilts the support through a specific angle relative to a horizontal axis, the contrast medium commences to flow. In order to keep the flowing contrast medium at the isocenter the physician himself may conduct an adjustment of the support such that the x-coordinate of the respective examination point (location of the contrast medium) corresponds to the x-coordinate of the isocenter. The regulating device constantly determines, for the actual coordinates of the rotational center and the tilt angle $\alpha$, the height of the examination point and compares it with the reference or given height of the isocenter. The followup control ensures a constant adaptation of these two values.

With the aid of this automatic system it is advantageously possible, independently of the inclination of the support and independently of the displacement thereof, to adjust the height automatically such that the examination point is always disposed at the isocenter. In this manner, the following of the contrast medium can be traced in a simple and reliable fashion on the image detection device.

Since for many examinations it is sufficient for the examination point to approximately lie at the isocenter, in a further development of the invention it is provided that the actual value of the point associated with the patient support for coincidence with the isocenter be established as on a straight line at the distance d' relative to the support. For example, in the case of a spinal examination in lateral position of a patient, the spine approximately follows such a straight line. In the case of greater deviations, moreover the possibility exists of manually adjusting a new distance d' from section to section.

The automatic readjustment of the height of the patient support apparatus—on the basis of the straight line—involves the following considerations listed by way of example:

First, let a straight line L be assumed parallel to the support—at least to the part of the support which is of interest for the examination—through the horizontal spatial axis about which the support is tilted. This parallel line L is established by the coordinates of the spatial tilt axis and the tilt angle. Furthermore, it is assumed that the examination point moves along a parallel line L' parallel to the support and hence to the imaginary line L through the horizontal spatial tilt axis. The distance between the two parallel lines L and L' can be differently selected at any time. First, a desired distance between the two parallel lines is ascertained. Thus, all values are specified in order for the coordinate values of the horizontal spatial pivot axis—occurring and measured during the examination—to determine the respective actual coordinate of the examination point in the y-direction. Such actual coordinate for the examination point can then be compared with the isocenter coordinate in the y-direction.

In an advantageous further development of the invention, a microprocessor is provided as control device which, from the input values, determines the actual value for the y-coordinate of the point associated with the patient support and, through a comparison with the corresponding isocenter coordinate value, generates the signal for a followup control which is supplied to the latter via a digital-to-analog converter. By basing the automatic height adjustment on the already-mentioned mathematical relationships, a microprocessor is particularly well suited for the control. The actual current measured values for the position of the horizontal spatial tilt axis and for the tilt angle can be read off in analog fashion and supplied to the microprocessor via analog-to-digital converters.

A particularly advantageous embodiment provides that, at least for the x-coordinate of the horizontal spatial tilt axis, a digital-coded position reader is provided whose signal can be directly supplied to the microprocessor.

A particularly space-saving and optimally accessible patient support apparatus for the physician results, in a further development of the invention, through utilization of a displaceable overhead support, known per se, with an arm for the support which is adjustable in height. This patient support apparatus is particularly advantageously combined with an x-ray apparatus mounted on a C-arc support, which x-ray apparatus can directly contain arrangements for the determination of the reference values defining the position of the isocenter.

In the following, the invention shall be explained in greater detail on the basis of an exemplary embodiment described in two Figures on the accompanying drawing sheets; and other objects, features and advantages will be apparent from this detailed disclosure and from the appended claims.

BRIEF DESCRIPTION OF THE DRAWING

FIG. 1 shows, in a schematic illustration, the inventive patient support apparatus with the automatic height adjustment; and FIG. 2 shows, in perspective illustration, a diagrammatic section of the patient support apparatus in conjunction with an x-ray apparatus.

DETAILED DESCRIPTION

The patient support apparatus 1 according to FIG. 1 possess a column 3, displaceable on the ceiling 2, on whose telescopically extensible arm 4 a support 5 for a patient 6 is rotatably mounted. The support 5 is here illustrated as a continuous bed. However, it is likewise possible for this support to be constructed, in a known fashion, from hinged parts. The height adjustment of the support arm 4 proceeds by means of a motor 7. The tilting of the support about its rotational axis (horizontal spatial tilt axis) 8 here proceeds by means of a motor 9. The displacement along the ceiling 2 proceeds manually. A coordinate system is indicated in FIG. 1 wherein the location of the rotational axis 8 is designated by coordinates relative to x and y axes. Connected with the column 3 is a potentiometer 10 for the determination of the coordinate of the rotational point 8. Furthermore, an angle generator system 11 is connected to this rotational point 8 for the determination of the angle $\alpha$.

In the exemplary embodiment according to FIG. 1, for the determination of the x-coordinate of the rotational point 8, a digital-coded position reader 12 is provide on the ceiling.

In this schematic view there is no detailed illustration of the design of the x-ray apparatus. It is merely illustrated in the form of a box 13 depicted in broken lines from which the reference coordinate values for the isocenter can be learned. (Further illustration of a preferred x-ray apparatus is found in FIG. 2.) On a control console 15, shown centrally of FIG. 1, by means of a potentiometer 16, via a control element 17, the motor 9 for the tilting of the support 5 can be activated. Likewise, from this control console, via a potentiometer 18 and a two-way switch 19, a followup control 20 for the motor 7, and hence for the height adjustment of the support, can be activated. Moreover, the control contains a switch 21 for starting up the automatic control system.

In the present exemplary embodiment, a microcomputer 22 serves as the control device. The measured values for the coordinates of the rotational center 8 and the angle of table 5 are references with $x_b$, $y_b$, and $\alpha$. The measured values for the isocenter are designated $x_a$ and $y_a$, having reference to the same coordinate system. Aside from the x-coordinate $x_b$ of the rotational center 8 all other values may be generated in analog form. Via lines 23, 24 and 25, the values $y_a$, $y_b$, as well as $\alpha$ are supplied via a multiplexer 26 and an analog-to-digital converter 27 to the microprocessor 22. The supply of the value $x_a$ is not illustrated in the Figure and may be assumed to be fixed during a fluoroscopic examination, for example. The $x_b$-value of the rotational center 8 is directly digitally measured and, via a line 28, can be directly supplied to the microprocessor. The microprocessor ascertains during the automatic system operation constantly the difference e between the actual value ($y_{is}$) and the reference value ($y_a$) of the isocenter ($e = y_a - y_{is}$). This value e is supplied via a digital-to-analogconverter 29 and the two-way switch 19 to the followup control 20 for the actuation of the motor 7.

The method of operation of the isocentric displacement of the inventive patient support apparatus is the following:

With a switched-off automatic system, the starting point of the examination, for example, the injection point for the contrast medium, is first brought into the isocenter (located at $x_a$, $y_a$). Subsequently, the automatic system is switched on. The microprocessor 22 first calculates the distance d between a parallel line L parallel to the support 5 and extending through the rotational point 8 and a line L' through the isocenter and parallel to line L. Subsequently, the microprocessor 22 continuously calculates the y-values ($y_{is}$) for the straight line L' at the location $x_a$ and forms the difference e between the isocenter reference value $y_a$ and the specific actual value $y_{is}$ (representing the point on the line L' at $x = x_a$). This difference value e forms the initial output value of the microprocessor 22 and is supplied via a line 30 to the digital-to-analog converter 29. The analog output signal of the digital-to-analog converter 29 is supplied via the two-way switch 19 to the followup control 20 in the form of input signal. If the ascertained actual value $y_{is}$ is greater than the isocenter reference value $y_a$ the support 5 is lowered. If the actual value $y_{is}$ is smaller than the isocenter reference value $y_a$ the support 5 is raised. Thereby, independently of how the support 5 is tilted or longitudinally displaced, the height is constantly so readjusted that relatively the isocenter ($x_a$, $y_a$) is displaced along the line L' (i.e. line L' continuously intersects the isocenter as the support is moved horizontally). The observation point of the body region under examination thereby always lies at the isocenter.

The line L parallel to the support 5 and extending through the horizontal spatial tilt axis 8 has a location which can be defined as a function of the coordinates of this spatial tilt axis $x_b$, $y_b$ and of the tilt angle $\alpha$ and the following relationship can be written:

$$-\sin \alpha \cdot x + \cos \alpha \cdot y - \cos \alpha \cdot y_b + \sin \alpha \cdot x_b = 0$$

The distance between this straight line L and the parallel line thereto L' which is extend through the isocenter is referenced with d and forms a constant which can be written in corresponding fashion as $$d = -\sin \alpha_o \cdot x_a + \cos \alpha_o \cdot y_a - \cos \alpha_o \cdot y_{bo} + \sin \alpha_o \cdot x_{bo}$$

whereby $\alpha_o$, $x_{bo}$ and $y_{bo}$ are the corresponding values for the start point of the automatic system. The distance between the support 5 and the parallel line thereto L' is referenced with d'.

Correspondingly, for the straight line L', the following equation results:

$$y = (1/\cos \alpha)(\sin \alpha \cdot x + \cos \alpha \cdot y_b - \sin \alpha \cdot x_b + d)$$

For $x = x_a$ hence the actual value $y_{is}$ may be expressed as:

$$y_{is} = (1/\cos \alpha) \cdot (\sin \alpha \cdot x_a + \cos \alpha \cdot y_b - \sin \alpha \cdot x_b + d)$$

In FIG. 2, in perspective illustration, a section of the patient support apparatus 1 is illustrated. Corresponding parts are provided with the same reference numerals. On the support 5 a patient 6, resting in lateral position, is illustrated. The support is rotatably mounted on a support arm 4 which is telescopically displaceable in a vertical direction in a ceiling supported column 3. In addition, an x-ray apparatus 13 with a known C-arc-support 40 for an x-ray tube 41 and an image detection device 42 is illustrated. Reference numeral 43 indicates the central ray between the focus of the x-ray tube 41 and the center of the image detection apparatus 42 which passes through the isocenter ($x_a$, $y_a$). If, for example, in the nape region, contrast medium is injected in the spinal cord channel, given the illustrated inclined position of the patient, the contrast medium flows slowly in the direction of the foot end of the patient 6 along the spinal cord channel.

This channel lies essentially in a plane (corresponding to a selected line 1") parallel to the support 5. With the aid of the described automatic system for the height adjustment it is therefore possible in the case of longitudinal displacement of the support 5 to always keep the contrast medium at the isocenter ($x_a$, $y_a$).

It will be apparent that many modifications and variations may be made without departing from the scope of the teachings and concepts of the present invention.

I claim as my invention:

1. In an x-ray examination system, an x-ray apparatus defining an isocenter, a patient support apparatus comprising a support rotatable about a horizontal spatial axis, for positioning a patient resting on said support, which support is height-, and horizontally adjustable relative to the isocenter of the x-ray apparatus, and motor means for effecting at least the height adjustment, the x-ray apparatus providing reference values representative of the position of the isocenter, the patient support apparatus further comprising one actual value transmitter each for supplying actual coordinate values respectively, representative of the position of the horizontal spatial axis, and an angle function generator for supplying an actual value representative of the tilting of the support, a processing device receiving the actual values and the reference values and supplying an output as a function of any vertical offset between an examining point at distance d' above the support and the isocenter, and a control coupled with the motor means for the height adjustment, which upon occurrence of a difference between the actual and reference values with respect to the isocenter in the vertical direction, activates the motor means for the purpose of reducing said difference.

2. An x-ray examination system according to claim 1, characterized in that the processing device derives an actual value for comparison with the vertical position of the isocenter, which is established as lying on a parallel line (L') at a distance d' above the support.

3. An x-ray examination system according to claim 1, characterized in that a microprocessor is provided as the processing device which, from the input values, ascertains an actual value for comparison with the vertical position of the isocenter and, through a comparison with a corresponding reference value, generates the output for the control and a digital-to-analog converter interposed between the microprocessor and the control.

4. An x-ray examination system according to claim 3, characterized in that analog-to-digital converter means is connected with the microprocessor at the input side thereof for the conversion of coordinate values in analog form.

5. An x-ray examination system according to claim 1, characterized by an overhead support, displaceable in a horizontal direction, and having an arm carrying the support which is adjustable in height.

6. An x-ray examination system according to claim 3, characterized in that, at least for sensing a horizontal coordinate value for the position of the horizontal spatial axis, a digital-coded position reader is provided whose signal is directly supplied to the microprocessor.

7. An x-ray examination system according to claim 1, characterized in that, for the tilting of the support, said motor means comprises an additional motor, and control means coupled with the additional motor and comprising a potentiometer for effecting tilting adjustment of the support.

8. An x-ray examination system according to claim 1, characterized in that the x-ray apparatus is mounted on a separate support and contains arrangements for the determination of the reference values of the isocenter with respect to horizontal and vertical coordinate axes.

9. A method for the isocentric displacement of a patient support apparatus which includes a patient support rotatable about a horizontal spatial axis, for positioning a patient resting on said patient support, which patient support is height-, and horizontally-adjustable relative to a specified isocenter of the patient support apparatus, and motor means for effecting at least the height adjustment of the patient support, the patient support apparatus further comprising one actual value transmitter each for suppling actual coordinate values respectively, representative of the horizontal and vertical position of the horizontal spatial axis, and an angle function generator for supplying an actual angle value representative of the tilting of the support, said method comprising:

(a) rotating said support about the horizontal spatial axis such that the support is tilted at an angle of inclination to the horizontal, and supplying an actual angle value from the angle function generator representative of the tilting of the support,
(b) generating reference values representative of the horizontal and vertical position of a specified isocenter of the patient support apparatus,
(c) supplying actual corrdinate values from the actual value transmitters representative of the horizontal and vertical position of the horizontal spatial axis,
(d) displacing the support in a horizontal direction while the support remains tilted at the angle of inclination,
(e) generating a regulating signal which is a function of the difference between the actual coordinate value from the actual value transmitter representing the vertical position of the horizontal spatial axis and the reference value representative of the vertical position of the specified isocenter, and
(f) automatically controlling said motor means to adjust the height of the patient support during horizontal movement of the patient support so as to tend to reduce the regulating signal such that the isocenter moves along a path relative to the patient support facilitating a desired patient examination.

10. A method according to claim 9, characterized in that the isocenter moves relative to the patient support along a parallel line (L') at a distance d' from the patient support.

* * * * *